United States Patent [19]

Herzer et al.

[11] Patent Number: 5,163,013
[45] Date of Patent: Nov. 10, 1992

[54] DEVICE FOR MEASUREMENT OF ULTRASONIC TRANSIT TIMES

[75] Inventors: Rudiger Herzer, Saarbrucken; Eckhardt Schneider, Riegelsberg, both of Fed. Rep. of Germany

[73] Assignee: Fraunhofer-Gesellschaft zur Forderung der angewandten Forschung E.V., Munich, Fed. Rep. of Germany

[21] Appl. No.: 485,143

[22] Filed: Feb. 26, 1990

[30] Foreign Application Priority Data

Feb. 25, 1989 [DE] Fed. Rep. of Germany ....... 3905956

[51] Int. Cl.⁵ .............................................. G01B 17/02
[52] U.S. Cl. .................................. 364/563; 364/569; 377/20
[58] Field of Search ..................... 328/129.1; 364/569, 364/563; 377/20

[56] References Cited

U.S. PATENT DOCUMENTS

| | | | |
|---|---|---|---|
| 3,690,154 | 9/1972 | Wells et al. | 73/615 |
| 4,164,648 | 8/1979 | Chu | 377/20 |
| 4,303,983 | 12/1981 | Chaborski | 377/20 X |
| 4,452,085 | 6/1984 | Pelc et al. | 73/631 |
| 4,685,075 | 8/1987 | Morita et al. | 377/20 X |
| 4,715,008 | 12/1987 | Jones | 364/563 |
| 4,931,965 | 6/1990 | Kaneko et al. | 364/560 |
| 4,982,350 | 1/1991 | Perna et al. | 364/569 |
| 4,996,474 | 2/1991 | Tambe et al. | 364/484 X |

FOREIGN PATENT DOCUMENTS 0295893 12/1988 European Pat. Off. .
2853170 6/1980 Fed. Rep. of Germany .

OTHER PUBLICATIONS

"New, Compact Instrument for Pulse-Echo-Overlap Measurements of Ultrasonic Wave Transit Times" by Emmanuel P. Papadakis, Rev. Sci. Instrum., vol. 47, No. 7, pp. 806–813 (1976).

"A digital Electronic Instrument for Measuring Sound Velocity" by G. Carini and F. Mento, J. Phys. E:Sci. Instrum., vol. 12, pp. 259–260 (1979).

"An Apparatus for High Precision Measurements of Ultrasonic Wave Velocity" by Y. K. Yogurtcu et al., Ultrasonics, Jul. 1980 pp. 155–159.

Primary Examiner—Parshotam S. Lall
Assistant Examiner—Edward R. Casimano
Attorney, Agent, or Firm—Baker & Daniels

[57] ABSTRACT

A device for measuring ultrasound transit times in workpieces disposed over an HF pulse generator which generates high-frequency wave trains with few oscillations periods and which is connected with an ultrasound transmitter/ultrasound receiver, whose output signal acts upon a comparator. The comparator generates pulses on zero crossings of the ultrasound echo. Between a gate circuit and a counter there is provided an AND-gate, whose second input is acted upon with the output signal of the comparator. The time gate of the gate circuit can be positioned, computer controlled, a quarter-wavelength of the ultrasound before the maximum of the envelope curve signal of the amplified ultrasound echo, so that it always equal-lying steepest zero crossing triggers the start or stop impulse of the counter. The time gate is positioned at a fixed time spacing to the time point A given by the threshold value, so that through the envelope curve transit time variations affecting as a whole, for example in the case of a conical widening of the workpiece to be detected, the time gate still surely detects the zero crossing to be separated.

9 Claims, 3 Drawing Sheets

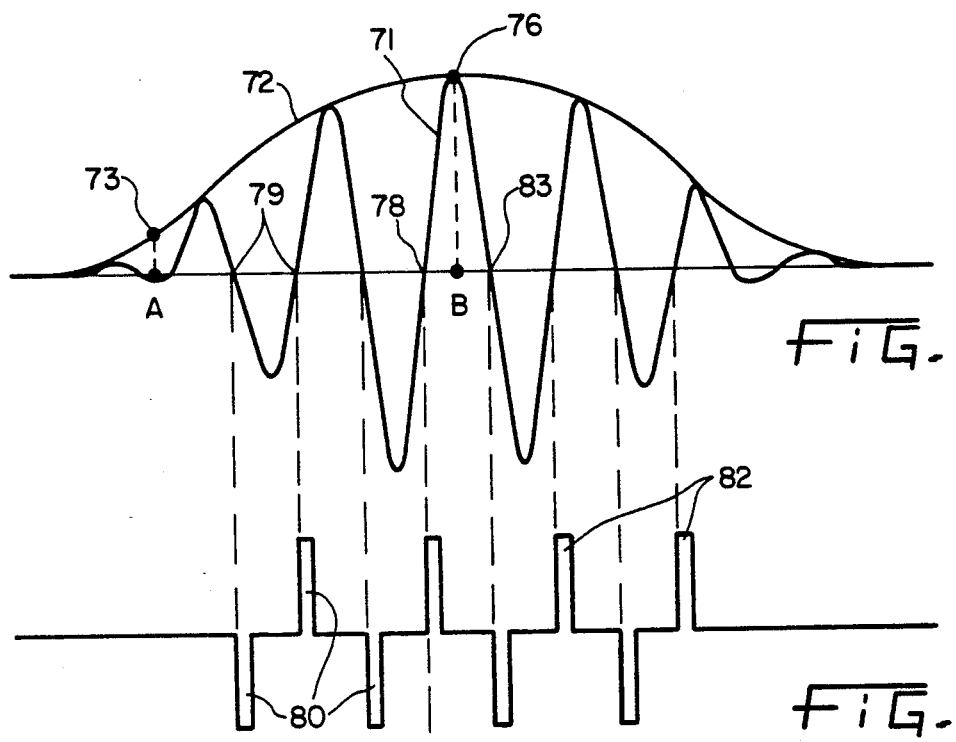
FIG. 4A
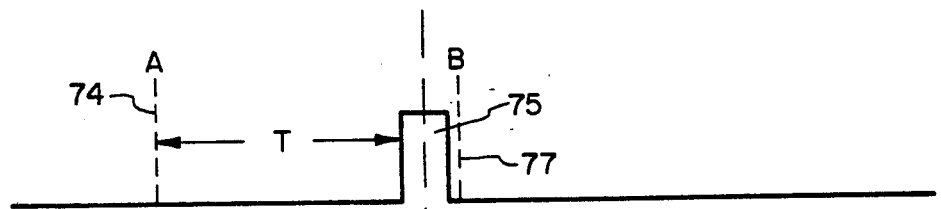
FIG. 4B
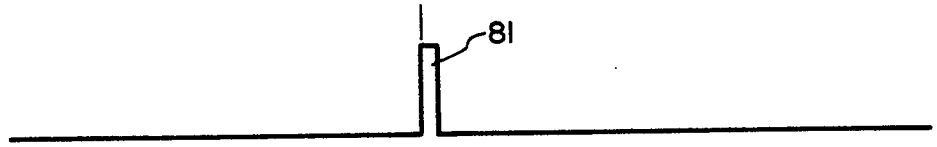
FIG. 4C
FIG. 4D
FIG. 4E

DEVICE FOR MEASUREMENT OF ULTRASONIC TRANSIT TIMES

BACKGROUND OF THE INVENTION

The invention relates to a device for the measurement of ultrasonic transit times in workpieces with an HF pulse generator which generates high-frequency wave trains with few oscillation periods. The HF pulse generator is connected with an ultrasonic transmitter which is in coupling contact for ultrasound transmission with the workpiece to be examined. An ultrasonic receiver is likewise in coupling contact for ultrasound reception with the workpiece to be examined. The output signal of the receiver acts on a zero-crossing comparator and on a gate circuit. A synchronization input of the gate circuit is connected with the HF pulse generator. The gate circuit is connected to the first input of an AND-member with the start/stop input of a counter. The second input of the AND-member is connected with the output signal of the zero-crossing comparator and the time gate of the gate circuit is positionable on predetermined zero crossings.

For the characterization of material joints and states there are used ultrasonic processes in which the elastic interaction between the ultrasonic wave passing through the workpiece and the material is utilized. The measurement is the transit time of the ultrasonic wave. By very precise detection of these transit times, with exact knowledge of the spatial formation of the workpiece, mechanical tension states can be determined in components, textures in rolling products or also the porosity of ceramics.

A prior art device of this type is known from the U.S. journal Ultrasonics, vol. 26, No. 5, pp. 256–258 (1988), in which the received ultra-sound echoes are resolved with a zero voltage comparator into a pulse sequence In the time space of the entry of the first ultrasonic echo., the second ultrasonic echo, or a further ultrasonic echo, in each case a time gate with adjustable gate width is positioned. From the large number of zero crossing impulses of the first ultrasound echo a zero crossing is selected and a counter is started. From the large number of zero crossing impulses of the second or of a further ultrasound echo another zero crossing is selected and the counter is stopped. This prior art device for the measurement of ultrasonic transmit times has the disadvantage that for a given measuring arrangement the gates must be manually adjusted In case the ultrasonic transit times change to a relatively great degree, the selected zero crossing impulse leaves the preadjusted gate and the device interrupts the measurement value detection.

If the material to be examined or the testing head is changed, the parameters of the gates must be manually redetermined and stored. This time-intensive process must likewise be carried out on a change of the sample thickness of the material to be examined.

The U.S. Journal Rev.Sci.Instrum., Vol. 51, pp. 355–356 (1980) teaches a similar device for the detection of ultrasound transit times with a zero crossing detector, in which the gate circuit is to be positioned manually by the operator with the aid of an oscilloscope.

From U.S. Pat. No. 3,690,154 there is known a device for the thickness determination of materials, which, with the aid of a tunnel diode, selects the first zero crossing of an ultrasound echo and uses it for the Starting and stopping of a counter. Such a device has the disadvantage of a low measuring accuracy, since the signal-to-noise ratio at the first zero crossing of the echo signal is relatively poor.

U.S. Pat. No. 4,452,085 describes a counting arrangement for an ultrasound scanner. A zero voltage detector counts the incoming echo pulses of a predetermined time segment over the number of which there is found the spectral attenuation of the reflected ultrasound in the sound-treated medium.

Another device for detecting ultrasound transit times is described by Moro, Farina and Rossi in the journal NDT-International, p. 169, Aug. 1980. An ultrasound wave of a few wave trains is generated by an excitation of a piezoceramic transformer with the aid of an HF transmitter. The ultrasound wave entering the workpiece generates by reflection of the workpiece back sides a first echo, and in sequence, a second and further echoes, which are received by the ultrasound receiver and amplified in the amplifier engaged on the outlet side.

In the gate circuits of the known devices, with the aid of synchronization impulses of the HF transmitter there are generated time gates with which the successively entering ultrasound echoes are coincident and generate starting and stopping impulses for the connected high-frequency counter. The overstepping of a threshold value of the amplified ultrasound signals is used for the starting and stopping of the time counter.

With this measuring method amplitude fluctuations which can arise through change of the coupling of the ultrasound transmitter or ultrasound receiver onto the workpiece to be investigated, through joint changes or by sound-bundle divergences, can lead to considerable errors in the time measurement. In the state of the art, through the errors arising here, it is not possible to make transit time measurements accurate to nanoseconds between two ultrasound echoes in an industrial environment.

SUMMARY OF THE INVENTION

Underlying the invention is the problem of creating a device of the type mentioned which makes it possible to perform transit time measurements accurate to nanoseconds of ultrasound echoes with arbitrary testing heads, materials and sample thickness in rapid sequence.

This problem is solved according to the invention by providing an envelope curve demodulator between the output of the ultrasound receiver and the gate circuit. The output signal of the ultrasound receiver acts upon a maximum detector and a threshold value comparator whose output is connected with the gate circuit. The threshold value comparator generates an output signal at a predetermined low threshold value for a first time point at the beginning of the envelope curve. The maximum detector generates an output signal on the reaching of the maximum of the envelope curve signal at a second time point. In the system the first time point establishes the earliest time point and the second time point establishes an orientation point in the form of the latest time point of the time gate. By means of a delay control circuit the delay of the time gate of the gate circuit is adjustable for a time spacing of M quarter-wavelengths of the ultrasound to the maximum value, in which M is an odd natural number.

Through the use of an envelope curve demodulator the output signal of which acts upon a threshold value comparator and a maximum detector, two characteristic time points in an ultrasound echo are determinable. In the first place, an approximately starting time point of the ultrasound echo and, in the second place, the maximum of the envelope curve of the reflected ultrasound echo are deteriorable. The first time point gives the earliest time point and the second time point the latest time point for the time gate to be positioned by a delay control circuit. The delay control circuit sets in the delay of the time gate of the gate circuit in time, for example, by a quarter of the wavelength of the ultrasound before the maximum. Therefore the last zero crossing of the ultrasound echo is surely selected before the maximum of the wave train of the ultrasound which presents the greatest steepness and therewith the best signal-to-noise ratio of the ultrasound wave train. The time gate is present, therefore, at a predetermined spacing from the earliest time point and, therefore, in the same time position in each ultrasound echo, so that the time gates are automatically shifted along in new measurements with other samples or changing sample thicknesses as the ultrasound echo changes in time.

The selection of the correct zero crossing is derived from the ultrasound echo itself. Thereby, for example, in comparison with the selection of the zero crossing over a synchronization impulse of the HF transmitter, errors through ultrasound transit times of multiples of the half transmission wavelength are avoided.

BRIEF DESCRIPTION OF THE DRAWINGS

An example of execution of the invention is explained in detail with the aid of the drawings, wherein:

FIGS. 4a-4e show signal courses of various output signals of the device for measuring ultrasound transit times in workpieces.

DESCRIPTION OF THE PREFERRED EMBODIMENT

Figure 1:
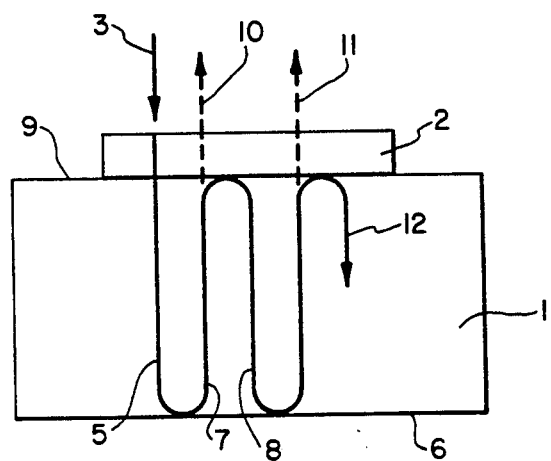
FIG. 1 shows a workpiece to be investigated with an emplaced ultrasound transmitter and ultrasound receiver.

FIG. 1 schematically shows a workpiece 1 to be examined, with an ultrasound transmitter and ultrasound receiver 2 emplaced thereon. The coupling contact between ultrasound transmitter and ultrasound receiver 2 and the workpiece 1 can be brought about, for example, also over a coupling layer of water or oil. The entry arrow 3 clarifies power fed to the combined ultrasound transmitter and ultrasound receiver 2 of an HF transmitter not represented in the drawing. The HF transmitter emits at periodic time intervals high frequency signals consisting of a few wave trains. These signals consisting of a few oscillation periods are transformed in the ultrasound transmitter and ultrasound receiver 2 into ultrasound impulses, which penetrate into the workpiece to be examined. A solid line shows in schematic form the course of the first ultrasound wave 5 penetrating the workpiece 1. The wave is reflected on the sample back surface 6 lying opposite the ultrasound transmitter and ultrasound receiver 2 and returns as reflected ultrasound wave 7 to the sample surface 9. In consequence of interactions with the sample material of the workpiece 1 the wave is increasingly attenuated in its amplitude over the travel path.

The reflected wave 7 returns to the ultrasound transmitter and ultrasound receiver 2 and is reflected in part as second ultrasound wave 8 on the sample surface 9 facing the ultrasound transmitter. The remaining part emerges from the workpiece 1 through the sample surface 9 facing the ultrasound transmitter. This constituent as first ultrasound echo 10 is schematically represented with a broken line. The first ultrasound echo 10 is transformed in the ultrasound transmitter and ultrasound receiver 2 into an electrical signal to be further processed by the electronic system of the device for the measurement of ultrasound transit times.

The second ultrasound wave 8, like the first ultrasound wave 5, is reflected on the oppositely lying sample back surface 6 of the workpiece 1 to be examined, and this wave constituent generates in the ultrasound transmitter and ultrasound receiver 2 a second ultrasound echo 11. The third ultrasound wave 12 arising by reflection on the sample surface 9 of workpiece 1 facing the ultrasound transmitter generates through further reflections on the sample back surfaces 6 and the sample surfaces 9 third and further ultrasound echoes, the signal amplitude of which becomes smaller and smaller.

Instead of the combined ultrasound transmitter and ultrasound receiver 2 there can be provided an ultrasound transmitter on the sample surface 9 facing the ultrasound transmitter and an ultrasound receiver fastened to the oppositely lying sample back surface 6. Then the nonreflecting constituents of the first and second ultrasound wave 5 and 8 form the first and second ultrasound signal of the ultrasound echo 10 and 11, respectively.

Figure 2:
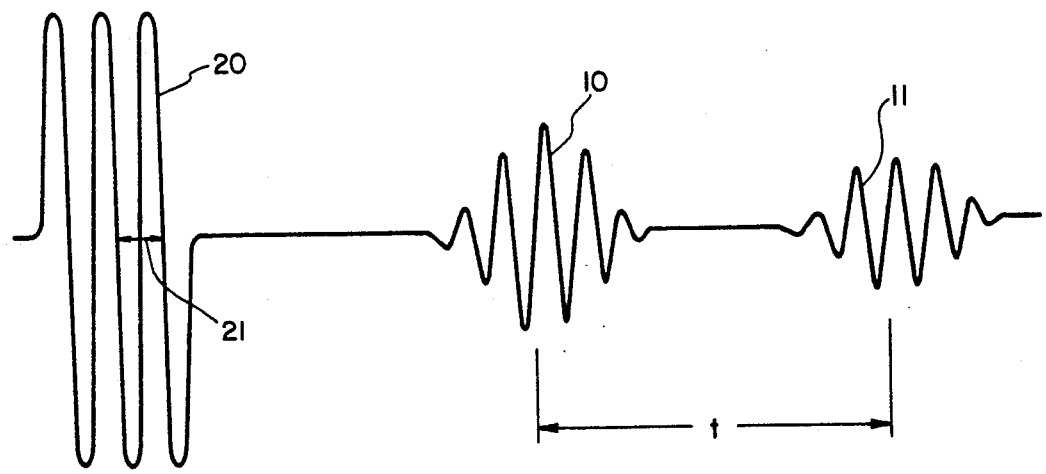
FIG. 2 shows the signal course of an electrical signal of an ultrasound impulse with ultrasound echo on the output of the ultrasound receiver.

FIG. 2 shows the time course of the electrical signal of an ultrasound impulse 20 and of the first ultrasound echo 10 and of the second ultrasound echo 11 at the output of the ultrasound receiver 2. The ultrasound impulse 20 consists of three high-frequency oscillation periods 21 with a constant, large signal amplitude. After a time which corresponds to the transit time required by the first ultrasound wave and the reflected wave 7 reflected on the oppositely lying sample back surface 6 in order to traverse the spatial distance between the sample surface 9 facing the ultrasound transmitter and the oppositely lying sample back surface 6. On the output of the ultrasound transmitter and ultrasound receiver 2 there appears the first ultrasound echo 10 and after the doubled transit time the second ultrasound echo 11. The echoes 10 and 11 present a considerably smaller amplitude and a bell-shaped envelope curves, whose maxima agree approximately with the centers of the echo signals 10 and 11.

In the case of a separate construction of ultrasound transmitter and ultrasound receiver, for example, the ultrasound receiver is arranged on the sample back surface 6 lying opposite the ultrasound transmitter 2. In such an arrangement the time between the ultrasound impulse 20 and the first ultrasound echo 10 is halved. The time difference between the first ultrasound echo 10, the second ultrasound echo 11 and all further echoes remains the same.

Figure 3:
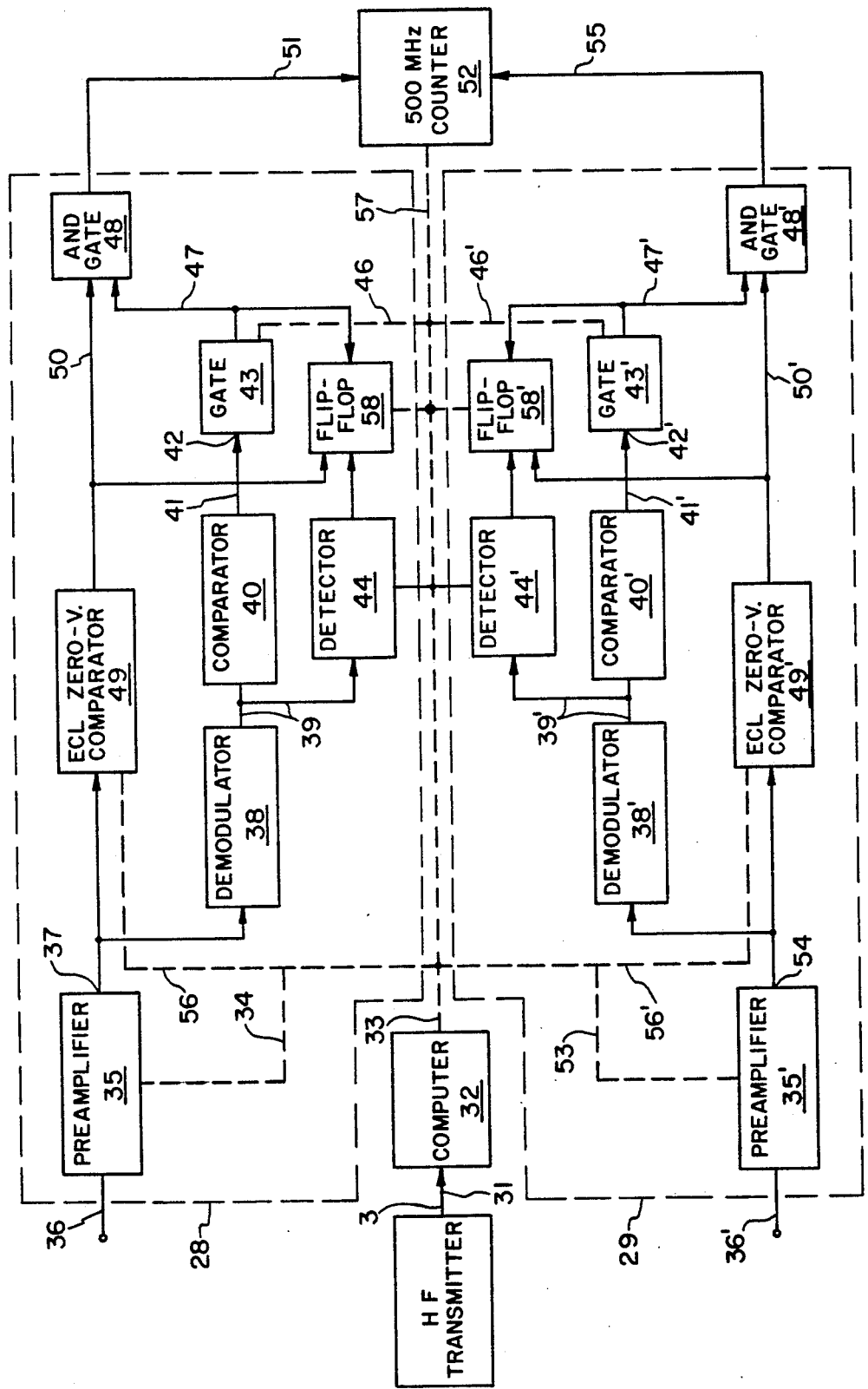
FIG. 3 is a block circuit diagram of a device for measuring ultrasound transit times in workpieces.

FIG. 3 shows a block circuit diagram of a device for measuring ultrasound transit times in workpieces. The circuit is subdivided into two like-constructed partial circuits, a start impulse circuit 28 and a stop impulse circuit 29, of which first the start impulse circuit 28 is described.

A synchronization signal output of the HF transmitter (not represented in FIG. 3) is connected over a synchronization line 31 with an electronic computer unit 32. The computer unit 32 disposes over a signal bus 33, over which a large number of the elements of the device described hereinbelow ar controlled.

The first signal bus lines 34 are connected to a preamplifier 35 which is connected with the ultrasound transmitter and ultrasound receiver 2 (not represented in FIG. 3) over a signal or synchronization line 36. The preamplifier 35 contains a gate switching circuit which is controlled with the aid of the first signal bus lines 34 of the computer unit 32. The gate switching circuit is open at the time point at which the first ultrasound echo 10 is presented to the preamplifier 35. The computer unit 32 calculates the opening duration of the time gate, which is greater than the duration of the ultrasound impulse 20 on the basis of the dimensions of the workpiece 1 to be investigated and of the synchronization impulse entering on the synchronization line 31, so that on the output 37 of the preamplifier 35 there is present only the amplified first ultrasound echo 71 represented in FIG. 4a. The computer unit 32 calculates, with knowledge of the oscillation period 21 of the high-frequency signal 20 and of the number of oscillation periods to be expected in the received first ultrasound echo 10, the opening duration of the time gate. On the basis of the overall dimensions of the workpiece 1 to be examined and with reference to the synchronization impulse arriving on the synchronization line 31, the time gate of the computer unit 32 can be enabled in such a way that on the output 37 of the preamplifier 35 there appears only the amplified first ultrasound echo 71 represented in FIG. 4a. Thus both the ultrasound impulse 20 and also the second or further ultrasound echoes 11 are suppressed.

For the clarification of the manner of functioning of the circuit in the following reference is repeatedly made to FIGS. 4a–4e, the reference numbers of which begin with 71. The amplified first ultrasound echo 71 acts upon an envelope curve demodulator 38, in which there is formed an envelope curve signal 72 of the amplified first ultrasound echo 71. This signal is presented over an envelope curve line 39 to a comparator 40. The comparator 40 is set on a threshold value 73 which is achieved in FIG. 4a at the time point A. The threshold value 73 is chosen in such a way that its amplitude lies only a little above the noise, so that even with great changes of the signal amplitude of the maximum value 76 of the envelope curve 72 the threshold value 73 lying on the lower portion of the envelope hardly changes.

The threshold value line 41 connected with the output of the comparator 40 is connected to a control input 42 of a gate circuit 43. The time point A conveyed over this line forms the earliest starting time point 74 represented in FIG. 4c for a time gate 75 of the gate circuit 43.

Over the envelope curve line 39 the envelope curve signal 72 likewise is presented to a maximum detector 44. Its output signal 84 represented in FIG. 4e gives the time point at which the amplified first ultrasound echo 71 reaches its maximum value 76. This output signal 84 is checked in a following flip-flop circuit 58 for time coincidence with the output of the gate circuit 43. The result of the checks is fed over the signal bus 33 to the electronic computer unit 32.

The output of the gate circuit 43 is connected, further, over a first coincidence line 47 with a dynamic AND-Gate 48.

The amplified first ultrasound echo 71 present on the output 37 of the preamplifier 35 acts also on an emitter-coupled logic (ECL) rapid zero-voltage comparator 49. This generates at zero crossings 79 of the amplified first ultrasound echoes 71 pulses 80, which are represented exaggeratedly wide in FIG. 4b. The pulses 80 act over the second coincidence line 50 on the dynamic AND-member 48.

The output of the ECL-zero-voltage comparator 49 acts likewise on the flip-flop circuit 58 and is checked for time coincidence with the output of the gate circuit. The result of this check is likewise transmitted to the electronic computer unit 32.

The output signal of the dynamic AND-member 48, which is represented in FIG. 4d, is for each ultrasound echo a single square impulse 81, which is yielded by the coincidence of the time gate 75 and the pulse 80 of a zero crossing 79. The electronic computer unit 32 separates the desired zero crossing, for example the last positive zero crossing 78 of the amplified first ultrasound echo 71 before its maximum 76. This zero crossing 78 presents the greatest pitch and, therewith the greatest signal-to-noise ratio.

The computer unit 32 sends over the signal bus 46 the opening time of the gate circuit 43 and therewith the width of the gate 75 in FIG. 4c with knowledge of the wavelength 21 of the high-frequency signal 20 for the entire measuring duration at approximately half the wavelength 21.

Further, over the signal bus 56 the zero voltage comparator 49 is adjusted in such a way that only positive zero crossings, i.e. positive pulses 82, still reach the AND-gate 48 engaged on outlet side.

Proceeding from time point A in FIG. 4c the computer unit 32 increases the delay time T of the gate circuit 43 from T=0 onward, beginning with the repetition frequency of the HF-transmitting signal and continuously checking in the flip-flop stage 58 the time coincidence of gate 75 and the maximum signal 84. If the gate comes to lie over the maximum 76 of the first ultrasound echo, the increment formation of T is terminated. The computer unit 32 now diminishes the delay time T until there is reported back to the computer unit 32 a time coincidence between, for example, a positive zero crossing 82 and the gate 75. This decrement or increment formation amounts to M times a ¼-wavelength 21, M representing an odd natural number.

Thus, for example, the desired separation of the zero crossing 78 is achieved and therewith the generation of the square impulse 81.

It is possible in the determination of the start impulse or of the stop impulse also to limit oneself to the zero crossing 83 with negative pitch following the maximum 76 of the envelope curve 72. The maximum detector 44 detects the time point B and the maximum signal acting on the computer unit 32 generates in the computer unit 32 a switching impulse which positions the time gate 75 a quarter-wavelength of the ultrasound after the maximum 76 of the envelope curve signal 72 of the amplified ultrasound echo 71.

The square pulse B1 is presented over a start line 51 to a 500-megahertz counter 52 and starts the same.

The stop impulse circuit 29 is constructed analogously to the already described start impulse circuit 28. Correspondingly, its electronic components are designated with the same reference numbers provided with an apostrophe. The electronic computer unit 32 controls over the second signal bus lines 53 the time gate of the second preamplifier 35', so that on the output 54 of the second preamplifier 35' there lies only the amplified ultrasound echo. Both the ultrasound impulse 20 and also the first, third or further ultrasound echoes are suppressed. The second ultrasound echo 11, somewhat weaker in comparison with the first ultrasound echo 10, is amplified in the second preamplifier 35' in such a way that its processing in the stop impulse circuit 29 occurs analogously to the processing of the amplified first ultrasound echo 71 in the start impulse circuit 28. The stop line 55 connected with the counter 52 presents a square stop impulse at the time point of the last zero passage before the maximum of the amplified second ultrasound echo.

With the 500-megahertz counter 52 the transit time of the ultrasound with a single HF transmitting impulse of the HF transmitter can be measured accurately to two nanoseconds. By averaging over a large number of HF transmitting impulses which can follow one upon another in the kilohertz range, the accuracy of the measurement is improved in the range of a few hundred picoseconds.

If a limitation is made as described to zero crossings 79 with positive pitch 82, then the variation of the trigger time point A which is evoked by amplitude fluctuations may amount to up to half the wavelength of the ultrasound. This yields a sufficient security for industrial measurements with moved ultrasound transmitters and ultrasound receivers 2 and coupling fluctuations evoked thereby, when the width of the time gate 75 gate is set on a small ultrasound wavelength or a wavelength 21 equal to half the ultrasound wavelength 21. The width of the pulses 80 is less than the width of the time gate 75.

There is measured, accordingly, the ultrasound transit time t in FIG. 2 between a first ultrasound echo 10 and a second ultrasound echo 11. There can be dependably measured there also changes of the transit time t which are substantially greater than a wavelength 21, since the gate 75 is held over the delay lines at a constant time interval from the time point A. With constant signal form of the ultrasound echo, the pulses 80 lie at an equal distance from the time point A, so that the separated signal, for example 81, does not change its relative position to the time point A, and thus surely remains within the gate 75. Therewith it is possible without interruption of measuring to measure, for example, conically increasing parts, since with such geometrically conditioned transit time changes the envelope curve with the time point A is shifted in its entirety and thus the separated signal 81 remains in the same position to the gate 75. There, amplitude fluctuations of the ultrasound echoes 10 and 11 likewise have no influence on the measurement, since the threshold point 73 establishing the time point A is predetermined on the flat lower portion of the envelope curve 72. It is only in the case of amplitude changes in the envelope curve 72, which lead so such a displacement of the phase position of the time point A and to the threshold point 73, that the gate 73 is shifted by a time corresponding to more than half an ultrasound wavelength that the electronic computer unit 32 interrupts the measurement. Such a phase change is associated mostly with anomalies in the workpiece, so that the measuring process is then broken off with the result of an unusual workpiece feature.

There likewise exists the possibility of carrying out ultrasound transit time measurements between arbitrarily selectable ultrasound echoes 10, 11 or between different zero crossings 79 of the same or of two different ultrasound echoes.

The electronic computer unit 32 can also be used to measure the transit times between different zero crossings 79, which change in each case by a half period of the ultrasound wavelength abruptly, as the gate 75, proceeding from the orientation time point B in FIG. 4c can be moved over each zero crossing before or after the time point B. The measured transit times are then averaged by computer.

In the example of execution described there is provided a start impulse circuit 28 and a stop impulse circuit 29, which process the first ultrasound echo 10 and the second ultrasound echo 11, respectively. The signal separation of the two echoes 10 and 11 occurs through delay members or computer-controlled in the electronic computer unit 32, which drives the preamplifier 35. In an advantageous embodiment of the invention the ultrasound transmitter emits two differently polarized ultrasound waves which are captured by an ultrasound receiver presenting two reception channels. The ultrasound signals arriving at a small time spacing are received separately in the two circuits 28 and 29 and permit a highly precise resolution of the time intervals between two of their zero crossings 79.

It is also possible to provide only the stop impulse circuit 29, which then generates the stop impulse for the counter 52. The start impulse is obtained in this case from the synchronization signal 31 of the ultrasound transmitter. The evaluation of the individual impulses as start impulses and stop impulses, which lie successively in time on the common start/stop input of the counter 52 occurs over a further synchronization line of the HF transmitter to the counter 52.

What is claimed is:

1. A device for measuring ultrasound transit times in workpieces, the device comprising:
    an HF pulse generator which generates high-frequency wave trains with few oscillation periods;
    an ultrasound transmitter connected with said HF pulse generator, said ultrasound transmitter being in coupling contact for ultrasound transmission with the workpiece to be examined;
    an ultrasound receiver having an output signal, said ultrasound receiver in coupling contact for ultrasound reception with the workpiece to be examined;
    a start impulse circuit coupled to the output signal of said receiver, said impulse circuit comprising:
        an envelope demodulator generating an output signal;
        a maximum detector having an input, said input receiving said envelope demodulator output signal;
        a threshold value comparator having an input and an output, said input receiving said envelope demodulator output signal;
        a zero-crossing comparator having an output;
        a gate circuit having a time gate positionable on predetermined zero crossings, an output, a synchronization input connected to said HF pulse generator, and an input connected to the output of said threshold value comparator;
        a delay control circuit coupled to said gate circuit for establishing the delay of the time gate of the gate circuit for a time interval of M quarter wavelengths of the ultrasound echo wave at the maximum, M being an odd natural number;

an AND-gate having a first input, a second input, and an output, said output of said gate circuit coupled to said first input of said AND-gate, and said output of said zero-crossing comparator coupled to said second input of said AND-gate; and a counter having a start/stop input, said output of said AND-gate coupled to said start/stop input;

wherein said threshold value comparator generates an output signal at a predetermined small threshold value at a first time point at the beginning of the envelope and the maximum detector generates an output signal at the maximum value of the envelope curve signal at a second time point, whereby the first time point establishes an earliest time point and the second time point establishes an orientation point in the form of the latest time point of the time gate, whereby the transit time in the workpiece is measured.

2. Device according to claim 1, wherein said time gate of the gate circuit is positionable by the delay control circuit by a quarter wavelength of the ultrasound echo wave before said maximum value.

3. Device according to claim 1, wherein a synchronization signal of the HF transmitter acts upon the counter and that the counter uses two signals fed to its start/stop input following the synchronization signal as start and stop impulses respectively.

4. Device according to claim 1, wherein a synchronization signal of the HF transmitter starts the counter, and that the counter uses the first signal appearing following the synchronization signal on its stop input as stop impulse.

5. Device according to claim 1, wherein a stop impulse circuit is provided through means comprising:
a second gate circuit;
a second zero-crossing comparator;
a second AND-gate;
a second envelope demodulator;
a second threshold value comparator; and
a second maximum value detector;
said stop impulse circuit interconnected analogously to said start impulse circuit, said start impulse circuit being connected only to the start input and the stop impulse circuit being connected only to the stop input of the counter.

6. Device according to claim 1, wherein at least one zero-crossing comparator is an emitter-coupled logic comparator.

7. Device according to claim 1, wherein the counter is a digital counter with a time resolution of at least two nanoseconds.

8. Device according to claim 1, wherein there is provided at least one preamplifier which is connected via a synchronization line with the HF transmitter and whose amplification is variable in dependence on the time spacing to a synchronization impulse for said time gates, whereby the ultrasound impulse is suppressed, and the amplification of the first ultrasound echo is less than that of the second ultrasound echo.

9. Device according to claim 1, wherein the ultrasound transmitter and the ultrasound receiver consist of a single transmitter/receiver unit.

* * * * *